ns of 4-(monoalkylamino)-
benzoic acids with hydroxyalkanoic acids and derivatives, phenols, or 3-pyridinols useful as hypolipidemic agents.

United States Patent [19]
Shepherd

[11] 4,196,208
[45] Apr. 1, 1980

[54] CERTAIN PYRIDYL ESTERS OF 4-(MONOALKYLAMINO) BENZOIC HYDROXYALKANOIC ACIDS

[75] Inventor: Robert G. Shepherd, South Nyack, N.Y.

[73] Assignee: American Cyanamid Company, Stamford, Conn.

[21] Appl. No.: 861,736

[22] Filed: Dec. 19, 1977

[51] Int. Cl.² ............... C07D 213/69; C07D 213/84; C07D 213/66; A61K 31/44
[52] U.S. Cl. .................................. 424/263; 424/266; 546/288; 546/294; 546/295; 546/314; 546/322; 546/296; 546/298; 546/300
[58] Field of Search ............... 260/295.5 R; 424/266, 424/263; 546/322, 314, 288, 294, 295

[56] References Cited

U.S. PATENT DOCUMENTS

| | | | |
|---|---|---|---|
| 3,786,060 | 1/1974 | Mardiguian et al. | 546/322 |
| 4,003,733 | 1/1977 | Johnston et al. | 71/94 |
| 4,132,784 | 1/1979 | Malhotra | 546/288 |
| 4,133,675 | 1/1979 | Schurter et al. | 546/288 |

*Primary Examiner*—Alan L. Rotman
*Attorney, Agent, or Firm*—Edward A. Conroy, Jr.

[57] ABSTRACT

This disclosure describes esters of 4-(monoalkylamino)-benzoic acids with hydroxyalkanoic acids and derivatives, phenols, or 3-pyridinols useful as hypolipidemic agents.

7 Claims, No Drawings

CERTAIN PYRIDYL ESTERS OF 4-(MONOALKYLAMINO) BENZOIC HYDROXYALKANOIC ACIDS

BRIEF SUMMARY OF THE INVENTION

This invention relates to new organic compounds and, more particularly, is concerned with novel 4-(monoalkylamino)-benzoate esters which may be represented by the following structural formula:

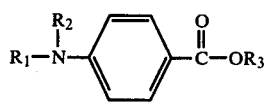

wherein $R_1$ is an unbranched or branched alkyl group of the formula $C_nH_{2n+1}$ where n is an integer from 8 to 19, inclusive; $R_2$ is selected from the group consisting of hydrogen or a group convertible in vivo thereinto such as methyl, carboxy-alkyl, acetyl, succinyl, 1-(sodiumsulfo)loweralkyl, 1-(sodium-sulfo)polyhydroxyalkyl, and 1,3-bis(sodiumsulfo)aralkyl or is an amine-protecting group such as trifluoroacetyl, carbobenzyloxy, tert-butyloxycarbonyl or the like; and $R_3$ is selected from the group consisting of unsubstituted or substituted aryl, unsubstituted or substituted heteroaryl, tetrahydropyranyl, and a substituted unbranched or branched (lower alkyl, cycloalkyl, loweralkenyl, or hydroxyloweralkyl)group consisting of 1–6 carbon atoms and bearing 1–3 substituents selected from the group consisting of carboxy, carboalkoxy, carboxamido, cyano, N,N-dialkylcarboxamido, and 2-dimethylaminoethoxycarbonyl.

Suitable branched alkyl groups for the substituent $R_1$ may be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,6,8-tetramethylnonyl, 1,4-dimethyl-1-ethylhexyl, 15-methylhexadecyl, 14-methylpentadecyl, 13,13-dimethyltetradecyl, 15,15-dimethylhexadecyl, and the like.

Suitable carboxyalkyl and sulfoalkyl groups for the substituent $R_2$ may be, for example, carboxymethyl, 2-carboxyethyl, 3-carboxypropyl, 1-sulfoethyl, 1-sulfopropyl and the like.

Suitable unsubstituted and substituted phenyl and 3-azaphenyl or 3-pyridyl groups for the substituent $R_3$ contemplated by the present invention are, for example, phenyl, 3-methylphenyl, 4-ethylphenyl, 3-bromophenyl, 4-fluorophenyl, 2,6-dichlorophenyl, 2,4-difluorophenyl, 3-carbomethoxyphenyl, 4-carboxyphenyl, 4-cyanophenyl, 4-carboxamidophenyl, 3-pyridyl, 5-methyl-3-pyridyl, 2,6-dimethyl-3-pyridyl, 6-methoxy-3-pyridyl, 2-hydroxy-3-pyridyl, 6-chloro-3-pyridyl, 4-carboxy-3-pyridyl, 4-cyano-3-pyridyl, and the like. Appropriate substituted loweralkyl, loweralkenyl, and hydroxyloweralkyl groups are those in which the alkyl or alkenyl group consists of 1–6 carbon atoms and is attached to the oxygen atom via a carbon atom which does not bear a hydroxy substituent, for example, carboxymethyl, methoxycarbonylmethyl, 1-methoxycarbonylpropyl, 1-ethoxycarbonylethyl, 2-cyanopropyl, 2-carboxyethyl, 1-dimethylcarbamoylethyl, 2-methoxycarbonyl-2-propyl, 2-carbamoyl-2-methylpropyl, 1,1-dimethylcarbamoylethyl, 2-ethoxycarbonylvinyl, 3-ethoxycarbonyl-1-propenyl, 2-carboxy-2-hydroxyethyl, 1,2-dicarboxyethyl, 1,2-di(ethoxycarbonyl)-2-hydroxyethyl, 1,2,3-tricarboxy-2-propyl, and the like.

The invention also pertains to novel compositions of matter and to methods of ameliorating hyperlipemia in mammals therewith; the active ingredients of said compositions of matter being the novel 4-(monoalkylamino)benzoic acid esters of the present invention. These compounds may be utilized either as the free bases or in the form of a pharmaceutically acceptable salt with an organic or inorganic acid or base. The invention also contemplates a method for lowering serum lipids in mammals by the administration of said esters.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nictonic acid [Levy and Frederickson, Postgraduate Medicine 47, 130 (1970)]. Clofibrate has the undesirable side-effect of causing hypertrophy of the liver in some patients.

The development of agents capable of reducng elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds of this invention are new and novel esters of the 4-alkylaminobenzoic acids described in U.S. Pat. No. 3,868,416 and have therapeutically useful biological and pharmacological properties. No hypolipemic activity has been reported in the literature for these compounds and they are different in structure and superior in action to other hypolipemic agents. The compounds of this invention lower serum-lipid concentrations and also decrease the deposition of lipids in the aorta. Esters such as these of hydroxy alkanoic acids, phenols, and 3-pyridinols are designed to facilitate the intestinal absorptive process and to provide a reliable and high degree of absorption following the oral administration required of hypolipidemic agents. To the extent that the α-OH carboxylic esters are hydrolyzed in the body they have the added advantage, relative to other esters, of producing hydroxyacids which are innocuous and are in many cases natural products or natural components of mammalian physiological processes. The novel esters of this invention are more reliably absorbed from the gastrointestinal tract than the carboxylic acids and many other esters. Also they cause less gastrointestinal irritation than the corresponding carboxylic acids.

We have now found that certain members of this class of compound can safely and effectively lower body serum sterols and triglycerides in warm-blooded mammals. Such actions on serum-lipid components are considered to be very useful in the treatment of atherosclerosis, especially in contrast to available drugs whose action is much more limited. For some time it has been considered to lower serum-lipid levels and to correct lipoprotein imbalance in mammals as a preventive measure against atherosclerosis. The compounds of the present invention do not act by blocking late stages of cholesterol biosyntheses and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic states found in patients with or prone to heart attacks, to peripheral or cerebral vascular disease, and to stroke.

The 4-(monoalkylamino)benzoate esters of the present invention are, in general, white crystalline solids having characteristic melting points and absorption spectra. They are soluble in organic solvents such as lower alkanols, chloroform, toluene, dimethylformamide, and the like but are generally not very soluble in water.

The novel 4-(monoalkylamino)benzoate esters of the present invention which are organic bases may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like. The esters which contain acidic groups form pharmaceutically acceptable salts with bases such as the alkali metals, the alkaline earths, and the like.

The novel compounds of the present invention may be readily prepared by treating an acid halide, mixed acid anhydride, or activated ester of the formulae:

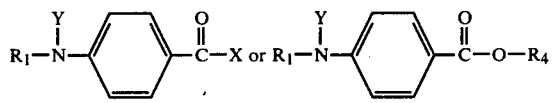

wherein X is chloro or bromo, R₄ is an activated ester or amide moiety or an acyl group and R₁ is as hereinabove defined with a hydroxy compound of the formula: HOR₃ wherein R₃ is as hereinabove defined. These reactions are preferably carried out in an inert solvent at a temperature of 25°–125° C. for a period of time from about 30 minutes to 18 hours or more. In the case of the acid halide and other acid-forming acylating agents, the reaction is carried out in the presence of an acid scavenger such as diisopropylethylamine, 4-dimethylaminopyridine, pyridine, triethylamine, finely powdered sodium carbonate, and the like. The acid halide and anhydride starting materials may be obtained from the corresponding 4-(monoalkylamino)benzoic acids by methods which are well-known in the art or described herein. However, a protecting group Y on the arylamino nitrogen is used for best results. The simplest protecting group is provided by double protonation of the amine to give an anilinium salt prior to or during formation of the acylating agent. Acylation of this amino group by carefully selected acyl groups such as carbobenzyloxy, carbo-t-butoxy, and trifluoroacetyl provides protection of this group from self-acylation during amide formation. These protecting groups are then removed by catalytic hydrogenation, mild acid treatment, and mild alkali treatment, respectively. Activated esters or amides, which are used to synthesize the esters of the present invention, are carboxymethyl, 4-nitrophenyl, N-oxysuccinimide, 1-imidazolyl and the like. In certain cases, treatment of acids or ordinary esters such as methyl or ethyl with an excess of an appropriate hydroxy-containing substrate in the presence of a Lewis or mineral acid such as boron trifluoride, sulfuric acid, or hydrochloric acid is sufficient to convert the 4-(monoalkylamino)-benzoic esters or acids to the appropriate esters.

With certain kinds of substrates for ester formation, it is necessary to form the alkali metal or strong organic base salts of the 4-(monoalkylamino)benzoic acids in order to react them with the various aforementioned halo-, methansulfonate- or p-toluenesulfonate-containing substrates. With certain β-carbonyl esters, it is necessary to preform the enol alcohol salt with an appropriate base such as sodium or potassium hydroxide, the alkali carbonates, or certain tertiary amines such as triethylamine, diisopropylethylamine, N,N-dimethylbenzylamine or the like, or in some cases, the copper salt of the enol form of the β-carbonyl ester can be employed to react with a suitably protected 4-(alkylamino)benzoic acid, activated for acylation, to form unsubstituted or substituted β-acrylates.

Certain 4-(monoalkylamino)benzoate esters may be prepared by the reaction of 4-(monoalkylamino)benzoic acids with diazoalkyl compounds such as ethyl diazoacetate and the like, obtained by reaction of nitrous acid or alkyl nitrite on α- or β-aminoalkanoate esters.

The 4-(monoalkylamino)benzoate esters are also prepared by reaction of the appropriate 4-aminobenzoate esters with suitable alkylating agents such as alkyl halides, sulfates, tosylates or trifluoromethanesulfonates with or without solvent at 50° C.-150° C. Suitable solvents are lower alkanols, chloroform, N,N-dimethylformamide, N,N-dimethylacetamide, diglyme, dimethylsulfoxide, acetonitrile, toluene, benzene, hexamethylphosphoramide and the like. The reaction may be carried out with an equivalent of base such as an alkali carbonate or bicarbonate, or with a catalytic amount of copper powder when alkyl halides are used as the alkylating agent.

Alternative methods of preparation are by reductive alkylation of a 4-aminobenzoate ester or by a metal hydride reduction of a 4-(acylamino)benzoate ester. For example, n-hexadecanal and ethyl O-[(4-aminobenzoyl)]glycolate are reduced under 1-10 atmospheres of hydrogen using an activated metal catalyst, forming ethyl [4-(hexadecylamino)benzoyl]glylcolate. Diborane reduction of certain 4-(hexadecanoylamino)benzoate esters at room temperature or above for 1-16 hours yields the corresponding 4-(hexadecylamino)benzoate esters.

Two types of substitution reactions also yield the 4-(monoalkylamino)benzoate esters, firstly, reaction of esters of 3,4-didehydrobenzoic acid with an alkylamine (or its alkali metal salt). Friedel-Crafts acrylation of an N-alkylaniline or N-acyl-N-alkylaniline also yields certain 4-(monoalkylamino)benzoate esters or intermediates thereto. The former type of reaction is carried out by treating a 4-halobenzoate ester such as phenyl 4-bromobenzoate with the lithium, potassium or sodium salt of excess alkylamine such as n-hexadecylamine in diethyl ether or other aprotic solvent. The second method comprises reacting N-hexadecylaniline and the like or its N-acetyl derivative with a carboalkoxy chloride and anhydrous aluminum chloride in dry diethyl ether, halocarbon or hydrocarbon medium.

The 4-(monoalkylamino)benzoate esters are also prepared by de-acylation of the corresponding 4-(N-trifluoroacetyl-alkylamino)benzoate ester by reacting with an alkali carbonate such as sodium or potassium carbonate in a lower alkanol, water or an aqueous lower alkanol at 5° C. to 50° C. Alternatively, the 4-(monoalkylamino)benzoate esters may be prepared by de-acylation of the 4-(N-carbo-t-butoxy-N-alkylamino)benzoate ester with mineral acids such as hydrochloric or hydrobromic acid, preferably in glacial acetic acid or with anhydrous trifluoroacetic acid at 0° C. to 50° C. Also, the 4-(monoalkylamino)benzoate esters are prepared by removal of the carbobenzyloxy protecting group from the anilino nitrogen atom by means of catalytic hydrogenation or treatment with a mineral acid such as hydrobromic acid, preferably in glacial acetic acid.

Certain derivatives

of the aminobenzoyl nitrogen atom are useful for providing greater solubility, more uniform and reliable intestinal absorption, and for a certain amount of modification of the pharmacology of the compounds of the present invention. Some of these derivatives can be converted to the corresponding N—H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like. The 1-(sodium sulfo)alkyl derivatives are obtained by reaction of the 4-(monoalkylamino)benzoate esters, or suitable intermediates in certain cases, with sodium bisulfite and an aliphatic aldehyde or a polyhydroxyaldehyde such as glyceraldehyde or glucose, and the 1,3-bis(sodium sulfo)aralkyl derivatives from cinnamaldehyde in a mixed organic-aqueous medium.

The glyceric acid esters of the present invention are prepared by careful oxidation of the 4-(alkylamino)-benzoyl glyceraldehyde esters; they can also be prepared directly by esterification of glyceric acid or by reactions using its 3-chloro or 2,3-epoxide analogs. The α-[4-(alkylamino)benzoyloxy]alkanoylamides can be prepared by reacting the appropriately protected and activated 4-(alkylamino)benzoic acid with a cyanohydrin followed by acidic hydrolysis, or by amination of an appropriate ester such as methyl or ethyl with a mono or dialkylamine, preferably in an alcoholic solvent. The amides can also be prepared by reacting the appropriate amide with an activated carboxylate ester.

The β-[4-(alkylamino)benzoyloxy]propionates are prepared by catalytic reduction at 1 to 10 atmospheres of hydrogen of the corresponding acrylate derivatives. They can also be prepared by treatment of β-halo, β-methanesulfonate, or β-p-toluenesulfonate alkanoates with the alkali salt of a 4-(alkylamino)benzoic acid in an inert solvent at 25° to 100° C.

The novel compounds of the present invention are potent hypolipidemic agents in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1

Preparation of 1-(methoxycarbonyl)propyl 4-(hexadecylamino)-benzoate

To a solution of 10.0 g. (24 m moles) 4-(hexadecylamino)benzoyl chloride hydrochloride in 200 ml. methylenechloride is dropwise added a solution of 3 g. (25.4 moles) methyl α-hydroxy butyrate and 5 g. (50 m moles) triethylamine in 100 ml. ether. After 17 hours stirring at room temperature, the precipitate is filtered and washed with several portions of ether. The ether solution is washed with water, dried, and condensed to the crystalline title compound.

EXAMPLE 2

Preparation of 1-(ethoxycarbonyl)ethyl 4-(hexadecylamino)-benzoate

To a warm mixture of 7 g. (18.3 m moles) sodium 4-(hexadecylamino)benzoate in 100 ml. ethanol is added 4.7 g. (18.3 m moles) ethyl α-tosyloxypropionate. After 17 hours at reflux, the cooled solution is diluted with an equal volume of water and the resultant precipitate is filtered. After washing with cold ethanol and drying, the product is crystallized from acetonitrile to yield the product as colorless crystals.

EXAMPLE 3

Preparation of 2-cyano-2-propyl 4-(hexadecylamino)benzoate

A stirred solution of 20 g. (48.0 m moles) 4-(hexadecylamino)benzoyl chloride hydrochloride in 500 ml. acetone and 50 ml. pyridine is cooled in an ice-water bath, and to this in portions is added 4.3 g. (51 m moles) acetone cyanohydrin. The solution is warmed to room temperature and stirred for an additional two hours. The solvents are evaporated to a yellow gum, which crystallizes to off-white crystals from ethanol.

EXAMPLE 4

Preparation of 1-carbamoylethyl 4-(hexadecylamino)benzoate

A mixture of 5 g. (12.1 m moles) 1-cyanoethyl 4-(hexadecylamino)benzoate in 100 ml. 75% sulfuric acid is heated at 50° C. for 20 hours. The cooled solution is diluted with water, filtered, and the residue is dried to yield the amide as a white amorphous solid.

EXAMPLE 5

Preparation of 1-carboxyethyl 4-(hexadecylamino)benzoate

A flask containing 10.0 g. (27.7 m moles) 4-(hexadecylamino)benzoic acid, 3.3 g. (36 m moles) lactic acid, 500 mg. toluenesulfonic acid and 500 ml. toluene is equipped with a Soxhlet extractor charged with activated 4A Linde molecular sieves. The solution is refluxed for 24 hours, during which time the Soxhlet extractor is charged twice more with fresh sieves. The hot solution is filtered and left to cool, whereupon the product separates as off-white crystals.

EXAMPLE 16

Preparation of 1-(chlorocarbonyl)ethyl 4-(hexadecylamino)-benzoate hydrochloride The amine hydrochloride is prepared by dissolving 6 g. (13.8 m moles) 1-carboxyethyl 4-(hexadecylamino)-benzoate into 100 ml. dimethoxyethane-methylene chloride (4:1) and passing dry hydrochloric acid gas through the cold solution until no additional precipitate is formed. To this is added 5 ml. (5 eq) thionyl chloride and the solution is refluxed until all precipitate has redissolved (about 1 hour). The solvents are evaporated to yield an orange, semi-crystalline mass of the acid chloride hydrochloride.

EXAMPLE 7

Preparation of 1-(dimethylcarbamoyl)ethyl 4-(hexadecylamino)-benzoate

To a solution of 3 g. (6.32 m moles) 1-(chlorocarbonyl)ethyl 4-(hexadecylamino)benzoate in 25 ml. pyridine is added 0.6 g. (7.5 m moles) dimethylamine hydrochloride. The solution is stirred at 50°0 C. for 15 hours, then evaporated to dryness. The residue is partitioned between 50 ml. water and 50 ml. methylene chloride. The layers are separated, and the aqueous solution is washed once more with 50 ml. methylene chloride. The combined organic solutions are dried, condensed, and the residue is crystallized from acetonitrile to yield the title compound as colorless crystals.

EXAMPLE 8

Preparation of 4-(hexadecylamino)benzoyl chloride hydrochloride

A cold solution of 25 g. (69.1 m moles) 4-(hexadecylamamino)benzoic acid in 500 ml. dimethoxyethane-methylene chloride (4:1) is prepared and dry hydrochloric acid is bubbled through the solution until no more precipitate forms. The solution is treated with 25 ml. (5 eq) thionyl chloride and refluxed until all of the precipitate has dissolved. The solvents are evaporated to yield an orange, semi-crystalline mass.

EXAMPLE 9

Preparation of N-trifluoroacetyl-4-(hexadecylamino)benzoyl chloride

To a stirred, ice-cold suspension of 9 g. (24.9 m moles) 4-(hexadecylamino)benzoic acid in 100 ml. dimethoxyethane and 16 ml. pyridine is treated with 18 ml. (5.2 eq) trifluoroacetic anhydride. The solution is stirred at 0° C. for 30 minutes at room temperature. The solution is diluted with 300 ml. ether and 100 g. ice. After stirring vigorously for 15 minutes, the phases are separated, the ether solution is washed with brine, dried and evaporated to a white, amorphous solid.

To 9.2 g. (20.1 m moles) of the above product in 30 ml. methylene chloride and 0.5 ml. dimethylformamide is added 5.7 ml. (80 m moles)thionyl chloride. After 20 hours at reflux, the solvents are evaporated to yield a light yellow, mobile oil.

EXAMPLE 10

Preparation of O-[4-(hexadecylamino)benzoyl]malic acid

To a warm solution of N-carbobenzyloxy-4-(hexadecylamino)benzoyl chloride and 1.3 g. (1 eq) triethylamine in 100 ml. ether is treated with 2 g. (14.9 m moles) malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% Pd(C) at 50 psi until hydrogen uptake stops. The catalyst is filtered, the solution is evaporated, and the residue is crystallized from acetic acid to yield the title compound as a tan, crystalline mass.

EXAMPLE 11

Preparation of diethyl O-[4-(hexadecylamino)benzoyl]malate

In a manner similar to Example 10, a solution of 6.0 g. (11.7 m moles) N-carbobenzyloxy-4-(hexadecylamino)-benzoyl chloride and 1.2 g. triethylamine in 100 ml. warm ether is treated with 2.3 g. diethylmalate. After one hour at relux, the precipitate is filtered off and washed with warm ether. After evaporation to dryness, the intermediate is dissolved in 50 ml. 30% hydrobromic/acetic acid and warmed at 50° C. for 2 hours. The solvents are evaporated and the product is partitioned between methylene chloride and water. The layers are separated and the methylene chloride is evaporated. The residue is crystallized from acetone to yield colorless crystals.

EXAMPLE 12

Preparation of diethyl O-[4-(hexadecylamino)benzoyl]tartarate

N-trifluoroacetyl-4(hexadecylamino)benzoyl chloride and 1.2 g. triethylamine in 100 ml. warm ether is treated with 2.5 g. (12.1 m moles) diethyl tartarate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the diethyl tartarate as a white, crystalline solid.

EXAMPLE 13

Preparation of 1-(carbamoyl)propyl 4-(hexadecylamino)benzoate

Into a solution of 4 g. (8.7 m moles) 1-(methoxycarbonyl)propyl 4-(hexadecylamino)benzoate in 50 ml. ethanol is bubbled ammonia gas until uptake ceases. The reaction is stirred at room temperature for 24 hours, then diluted with 100 ml. water. The precipitate is collected, washed with water, and dried. Crystallization from methyl cellosolve yields white crystals.

EXAMPLE 14

N-carbobenzyloxy-4-(hexadecylamino)benzoyl chloride

To 15 g. (41.5 m moles) 4-(hexadecylamino)benzoic acid in 200 ml. warm chloroform is added 15 g. sodium carbonate in 150 ml. water. To the vigorously stirred solution is added 10 g. (59 m moles) carbobenzyloxy chloride. After 2 hours stirring at 40° C., the layers are separated, washed three times with 1 N hydrochloric acid, dried, and evaporated to an oil. The oil is dissolved in 300 ml. toluene, treated with 15 ml. (5 eq) thionyl chloride and the solution is refluxed for 5 hours. The solvents are evaporated and the residue is dissolved three times in toluene, evaporating each time to yield a viscous, orange oil.

EXAMPLE 15

Preparation of 4-(N-t-butyloxycarbonyl-N-hexadecylamino)-benzoyl imidazole

To a solution of 10 g. (27.7 m moles) 4(hexadecylamino)benzoic acid in 100 ml. dioxane is treated with 4.0 g. (27.8 m moles) t-butylazidoformate and 10 ml pyridine. After sitrring at room temperature for 18 hours, the protected amidoacid is precipitated from solution by addition of 150 ml. water. The product was collected and thoroughly dried. The crude product is dissolved in 200 ml. of a mixture consisting of methylene chloride/dimethoxyethane/pyridine (1:4:1), and to this is added 5.4 g. (1.2 eq) 1,1'-carbonyldiimidazole. The solution is stirred overnight at room temperature and the solvents are evaporated to yield the title compound as a Thick, orange oil.

EXAMPLE 16

Preparation of 2-(ethoxycarbonyl)vinyl 4-(hexadecylamino)-benzoate

To a mixture containing 4.3 g. (8.33 m moles) 4-(N-t-butyloxycarbonyl-N-hexadecylamino)benzoyl imidazole, 50 ml. chloroform, and 50 ml. 5N sodium hydroxide is added 3 g. (2.4 eq) ethyl α-formyl acetate. The solution is vigorously stirred for 24 hours. The layers are separated, and the chloroform solution is washed once with 50 ml. 1N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 4-(hexadecylamino)benzoate.

EXAMPLE 17

Preparation of 1-cyanoethyl 4-(hexadecylamino)benzoate

A mixture of 1 g. (16.1 m moles) potassium cyanide, 5 ml. diisopropylethylamine and 800 mg. (18.1 m moles) acetaldehyde in 50 ml. tetrahydrofuran is stirred for 2 hours at room temperature. To this solution is added 6.7 g. (16.1 m moles) 4-(hexadecylamino)benzoyl chloride hydrochloride in 50 ml. tetrahydrofuran. After stirring for an additional 2 hours, the solution is diluted with 100 ml. water and extracted with ether. After drying the magnesium sulfate, the ether is evaporated and the residue is crystallized from acetonitrile to yield the title compound.

EXAMPLE 18

Preparation of 1-(ethoxycarbonyl)-2-propenyl 4-(hexadecyl-amino)benzoate

In a manner similar to Example 16, a solution of 5.3 g. (10.4 m moles) N-(t-butyloxycarbonyl)-4-(hexadecylamino)benzoylimidazole in 50 ml. dioxane is treated with 3.7 g. (1.15 eq) copper ethyl acetoacetate. After stirring at 40° C. for 24 hours, the solution is filtered and condensed. The residue is dissolved in 50 ml. warm (40° C.) trifluoroacetic acid, stirred for 2 hours, and again condensed. Crystallization from acetone yields the title compound as a colorless solid.

EXAMPLE 19

Preparation of 3-O-[4-(hexadecylamino)benzoyl]glyceric acid

To a solution of 3.6 g. (40 m moles) glyceraldehyde and 2.44 g. (20 m moles) 4-dimethylaminopyridine in an ice-water bath is added 11 m moles of N-trifluoroacetyl-4-(hexadecylamino)benzoyl chloride. After 4 hours, the product is partitioned between 50 ml. chloroform and 50 ml. water, and to the well-stirred solution is added 2 g. bromine and 1 g. sodium hydroxide. After thin-layer chromatography at intervals shows oxidation to be complete, the mixture is stirred 2 hours at 20° C. and the layers are separated. The organic layer is evaporated and the residue is crystallized from acetic acid to yield the title compound as a cream-colored, oily solid.

This ester is also prepared by employing glyceric acid in the procedures of Examples 16 and 17.

EXAMPLE 20

Preparation of 2-(ethoxycarbonyl)ethyl 4-(hexadecylamino)benzoate

A solution of 4 g. (8.7 m moles) 2-ethoxycarbonyl)vinyl 4-(hexadecylamino)benzoate and 400 mg. 10% Pd(C) in 100 ml. tetrahydrofuran is hydrogenated at 50 psi until hydrogen uptake stops. The catalyst is filtered, the solution is evaporated, and the residue is crystallized from acetonitrile to yield 2-(ethoxycarbonyl)ethyl 4-(hexadecylamino)benzoate.

EXAMPLE 21

Preparation of ethyl O-[4-(hexadecylamino)benzoyl]glycolate

A solution of 11.5 g. (30 m moles) sodium 4-(hexadecylamino)benzoate and 13.0 g. ethyl chloroacetate in 100 ml. hexamethylphosphoramide is heated at 125° C. for six hours, cooled, and diluted with 100 ml. water. The aqueous solution is extracted three times with 250 ml. ether. The combined ether layers are dried, diluted with 100 ml. methylene chloride and passed through a mixture of silica gel and aluminum. The product is crystallized from hexane and then from acetonitrile to yield light yellow products.

4-(Hexadecylamino)benzoic acid is slurried in mixed dimethoxyethane-methylenechloride solvent and stirred while adding an ethanolic solution of one molar equivalent of ethyl diazoacetate. The latter is prepared from treatment of ethyl glycinate in ethanol with one mole each of butyl nitrite and acetic acid.

EXAMPLE 22

Preparation of 4-chlorophenyl 4-(hexadecylamino)benzoate

To a solution of 6.4 g. (50 m moles) 4-chlorophenol and 7.6 g. (75 m moles) triethylamine in 500 ml. methylene chloride is added 10.4 g (25 m moles) 4-hexadecylamino)benzoyl chloride hydrochloride in 250 ml. methylene chloride. After four hours at reflux, the solution is cooled, washed with water and dilute phosphoric acid, and dried. After passing the solution through a column of alumina, the solvent is evaporated and the residue is crystallized from diisopropyl ether.

EXAMPLE 23

Preparation of tetrahydropyranyl 4-(hexadecylamino)benzoate

A mixture of 7 g. (19.4 m moles) 4-(hexadecylamino)benzoic acid, 2 g. (23.8 m moles) dihydropyran and 100 mg. anhydrous p-toluenesulfonic acid in 50 ml. toluene is stirred at room temperature for 20 hours. The solution is washed with saturated sodium bicarbonate, dried, and condensed. The residue is crystallized from methylcyclohexane to white crystals.

EXAMPLE 24

Preparation of 3-pyridyl 4-(hexadecylamino)benzoate

A 6 g. (16.6 m moles) sample of 4-(hexadecylamino)benzoic acid and 2.7 g. (16.6 m moles) 1,1'-carbonyldiimidazole in 50 ml. dry tetrahydrofuran is stirred for 2 hours. Then, 1.58 g. (16.6 m moles) 3-hydroxypyridine and a trace of sodium hydride catalyst is added and the reaction is refluxed for 3 hours. The solution is cooled, filtered, and evaporated. The product is crystallized from isopropanol.

EXAMPLE 25

Preparation of ethyl 4-(2,4,6,8-tetramethylnonylamino)-benzoate

A solution of 9 g. (34.2 m moles) 2,4,6,8-tetramethylnonylbromide, 6 g. (1.06 eq) ethyl 4-aminobenzoate, and 5 g. (1.05 eq) dry, powdered potassium carbonate in 50 ml. hexamethylphosphoramide is stirred at 120° C. for 17 hours. The cooled solution is diluted with 100 ml. water, the precipitate is filtered and washed with 100 ml. 50% aqueous ethanol. The product is dried and crystallized twice from ethanol to colorless crystals.

EXAMPLE 26

Preparation of ethyl 4-(1-ethyltetradecylamino)benzoate

Ten grams (43.8 m moles) 3-hydroxypentadecane and 4.9 g. (1.1 eq) triethylamine in 250 ml. methylene chloride is cooled to −10° C. in a dry ice-acetone bath. To the stirred solution is dropwise added 5.7 g. (1.1 eq) methanesulfonyl chloride in 10 ml. methylene chloride at a rate such that the reaction temperature does not exceed −5° C. After addition is complete, the solution is warmed to room temperature and washed in sequence with 100 ml. of the following ice-cold solutions: water, 10% hydrochloric acid, saturated sodium bicarbonate, and brine. The methylene chloride is dried and evaporated to a viscous, orange oil. Pentadecane-3-methanesulfonate (13.4 g. 43.7 m moles) and 14.4 g. (2 eq) ethyl 4-aminobenzoate in 75 ml. hexamethylphosphoramide is stirred at 120° C. for 18 hours. The cooled solution is diluted with 150 ml. water, the precipitate is filtered, washed with 150 ml. 50% aqueous ethanol and dried. Crystallization from ethanol and then from acetonitrile yields the product as a white solid.

EXAMPLE 27

Preparation of sodium 4-(14-methylpentadecylamino)benzoate

To a solution of 10 g. (27.7 m moles) 4-(14-methylpentadecylamino)benzoic acid in 300 ml. hot ethanol is added 6.0 ml. (1.1 eq) 5 N sodium hydroxide. As the solution cools, the title compound crystallizes as a white mass. This is collected and dried in vacuo.

EXAMPLE 28

Preparation of 4-(14-methylpentadecyl)aminobenzoic acid

A 4 g. (10.3 m mole) sample of ethyl 4-(14-methylpentadecyl)aminobenzoate is hydrolyzed with 2.0 g. (3 eq) 85% potassium hydroxide in 60 ml. 95% ethanol by refluxing the solution for 5 hours. The solution is cooled, diluted with 100 ml. water and acidified to pH 4.5 with 37% hydrochloric acid. The precipitate is collected and dried in vacuo to yield the title compound as a white powder.

EXAMPLE 29

Preparation of 15-methylhexadecylbromide

A solution of 3-methylbutylmagnesium bromide is prepared by treating 15 g. (0.1 mole) 3-methylbutyl bromide with 2.7 g. (1.1 eq) magnesium turnings in 50 ml. dry tetrahydrofuran. The resultant Grignard reagent is dropwise added to a cold (−10° C.) solution of 36.1 g. (1.1 eq) 1,12-dibromododecane and 0.2 g. (1 m mole) dilithiumtetrachloro cuprate in 75 ml. dry tetrahydrofuran. The solution is stirred for one hour, evaporated, and fractionally distilled in vacuo to yield 15-methylhexadecylbromide as a colorless liquid.

TABLE I

The following branched alkyl bromides are prepared following the method outlined in Example 29 and using the noted starting bromides.

| EX. NO. | STARTING BROMIDES | BRANCHED ALKYL BROMIDE PRODUCT |
|---|---|---|
| 30 | 3-methylbutyl bromide and 1,11-dibromoundecane | 14-methylpentadecyl bromide |
| 31 | t-butyl bromide and 1,12-dibromododecane | 13,13-dimethyltetradecyl bromide |
| 32 | 4,4-dimethylpentyl bromide and 1,11-dibromoundecane | 15,15-dimethylhexadecyl bromide |

TABLE II

The following ethyl 4-(branched and unbranched alkylamino)benzoates are prepared from the following alkyl starting materials as described in Examples 25 or 26 to yield:

| EXAMPLE | STARTING ALKYL COMPOUND | METHOD OF EXAMPLE | ETHYL 4-(ALKYLAMINO)-BENOZATE PRODUCT |
|---|---|---|---|
| 33 | 1-methylpentadecanol | 26 | Ethyl 4-(1-methylpentadecylamino)-benzoate |
| 34 | 1-heptylnonylbromide | 25 | Ethyl 4-(1-heptylnonylamino)-benzoate |
| 35 | 2-ethyldodecanol | 26 | Ethyl 4-(2-ethyldodecylamino)-benzoate |
| 36 | 1,4-diethyloctyl bromide | 25 | Ethyl 4-(1,4-diethyloctylamino)-benzoate |
| 37 | 11-methyldodecyl bromide | 25 | Ethyl 4-(11-methyldodecylamino)-benzoate |
| 38 | 5,5-dimethylhexyl bromide | 25 | Ethyl 4-(5,5-dimethylhexylamino)-benzoate |
| 39 | 4,8,12-trimethyltridecanol | 26 | Ethyl 4-(4,8,12-trimethyltridecylamino)benzoate |
| 40 | 1,4-dimethyl-1-ethyl hexanol | 26 | Ethyl 4-(1,4-dimethyl-1-ethylhexylamino)benzoate |
| 41 | 15-methylhexadecyl Bromide | 25 | Ethyl 4-(15-methylhexadecylamino)- |

TABLE II-continued

The following ethyl 4-(branched and unbranched alkylamino)benzoates are prepared from the following alkyl starting materials as described in Examples 25 or 26 to yield:

| EXAMPLE | STARTING ALKYL COMPOUND | METHOD OF EXAMPLE | ETHYL 4-(ALKYLAMINO)-BENOZATE PRODUCT |
|---|---|---|---|
| | | | benzoate |
| 42 | 14-methylpentadecyl bromide | 25 | Ethyl 4-(14-methylpentadecylamino)-benzoate |
| 43 | 13,13-dimethyltetradecyl bromide | 25 | Ethyl 4-(13,13-dimethyltetradecyl-amino)benzoate |
| 44 | 15,15-dimethylhexadecyl bromide | 25 | Ethyl 4-(15,15-dimethylhexadecyl-amino)benzoate |

TABLE III

The following 4-(branched and unbranched alkylamino)benzoic acids are prepared employing the method outlined in Example 28:

| EXAMPLE NUMBER | 4-(ALKYLAMINO)BENZOIC ACIDS |
|---|---|
| 45 | 4-(1-methylpentadecylamino)benzoic acid |
| 46 | 4-(1-heptylnonylamino)benzoic acid |
| 47 | 4-(2-ethyldodecylamino)benzoic acid |
| 48 | 4-(1,4-diethyloctylamino)benzoic acid |
| 49 | 4-(11-methyldodecylamino)benzoic acid |
| 50 | 4-(5,5-dimethylhexylamino)benzoic acid |
| 51 | 4-(4,8,12-trimethyltridecylamino)benzoic acid |
| 52 | 4-(2,4,6,8-tetramethylnonylamino)benzoic acid |
| 53 | 4-(14-methylpentadecylamino)benzoic acid |
| 54 | 4-(14-methylpentadecylamino)benzoic acid |
| 55 | 4-(15,15-dimethylhexadecylamino)benzoic acid |

TABLE IV

The following carboxmethyl-4-(alkylamino)benzoates are prepared according to the methods The acyl chlorides necessary for the method of Example 1 are prepared according to Example 8. The acyl chlorides necessary for the methods of Examples 10 and 11 are prepared according to the procedure of Example 14. The acyl chlorides necessary for the method of Example 12 are prepared according to Example 9, and the sodium salts required for the methods of Examples 2 and 21 are prepared by the procedure of Example 27.

| Example | Method According to Example No. | Reagent Used to Form Ester Moiety | Derivative of Carboxmethyl 4-(Alkylamino)Benzoate |
|---|---|---|---|
| 60 | 1 | methyl α-hydroxybutyrate | Methyl α-[4-(tridecylamino)benzo-yloxy]butyrate |
| 61 | 1 | Methyl α-hydroxybutyrate | Methyl α-[4-(nonylamino)benzoyl-oxy]butyrate |
| 62 | 1 | Ethyl α-hydroxybutyrate | Ethyl α-[4-(1-methyldodecylamino)-benzoyloxy]butyrate |
| 63 | 1 | Ethyl α-hydroxybutyrate | Methyl α-[4-(4,8,12-trimethyltri-decylamino)benzoyloxy]butyrate |
| 64 | 21 | Methyl chloroacetate | O-[4-(hexadecylamino)benzoyl]-glycolic acid (after mild alkaline hydrolysis) |
| 65 | 21 | Ethyl chloroacetate | Ethyl O-[4-(tridecylamino)benzoyl]-glycolate |
| 66 | 21 | Methyl chloroacetate | Methyl O-[4-(heptadecylamino)ben-zoyl]9 glycolate |
| 67 | 21 | Methyl chloroacetate | Ethyl O-[4-(1-heptylnonylamino)ben-zoyl]glycolate |
| 68 | 21 | Ethyl chloroacetate | Ethyl O-[4-(1,4-dimethyl-1-ethyl-hexylamino)benzoyl]glycolate |
| 69 | 21 | Ethyl chloroacetate | Ethyl O-[4-(15,15-dimethylhexadecyl-amino)benzoyl]glycolate |
| 70 | 2 | Methyl α-tosyloxypropionate | Methyl α-[4-(decylamino)benzoyloxy]-propionate |
| 71 | 5 | α-Hydroxypropionic acid | α-[4-(pentadecylamino)benzoyloxy]-propionic acid |
| 72 | 5 | α-Hydroxypropionic acid | α-[4-(nonadecylamino)benzoyloxy]-propionic acid |
| 73 | 5 | α-Hydroxyisobutyric acid | α-[4-(1-heptylnonylamino)benzoyl-oxy]isobutyric acid |
| 74 | 5 | α-Hydroxypropionic acid | α-[4-1,4-diethyloctylamino)benzoyl-oxy]propionic acid |
| 75 | 5 | α-Hydroxypropionic acid | α-[4-(15-methylhexadecylamino)ben-zoyloxy]propionic acid |
| 76 | 5 | α-Hydroxypropionic acid | α-[4-(13,13-dimethyltetradecyl-amino)benzoyloxy]propionic acid |
| 77 | 5 | α-Hydroxyisobutyric acid | α-[4-(1-methylpentadecylamino)ben-zoyloxy]isobutyric acid |
| 78 | 2 | Methyl α-tosyloxypropionate | Methyl α-[4-(1-heptylnonylamino)-benzoyloxy]propionate |
| 79 | 2 | Ethyl α-tosyloxypropionate | Ethyl α-[4-(13,13-dimethyltetra-decylamino)benzoyloxy]propionate |
| 80 | 10 | Malic acid | O-[4-(heptadecylamino)benzoyl] malic acid |

TABLE IV-continued

The following carboxmethyl-4-(alkylamino)benzoates are prepared according to the methods. The acyl chlorides necessary for the method of Example 1 are prepared according to Example 8. The acyl chlorides necessary for the methods of Examples 10 and 11 are prepared according to the procedure of Example 14. The acyl chlorides necessary for the method of Example 12 are prepared according to Example 9, and the sodium salts required for the methods of Examples 2 and 21 are prepared by the procedure of Example 27.

| Example | Method According to Example. No. | Reagent Used to Form Ester Moiety | Derivative of Carboxmethyl 4-(Alkylamino)Benzoate |
|---|---|---|---|
| 81 | 11 | Diethyl malate | Diethyl O-[4-(heptadecylamino)benzoyl]malate |
| 82 | 10 | Malic acid | O-[4-(decylamino)benzoyl]malic acid |
| 83 | 12 | Diethyl malate | Diethyl O-[4-(decylamino)benzoyl]malate |
| 84 | 12 | Diethyl tartarate | Diethyl O-[4-(5,5-dimethylhexylamino)benzoyl]tartarate |
| 85 | 12 | Diethyl tartarate | Diethyl O-[4-(2-ethyldodecylamino)benzoyl]tartarate |
| 86 | 11 | Diethyl malate | Diethyl O-[4-(1-methylpentadecylamino)benzoyl]malate |
| 87 | 12 | Citric acid | O-[4-(15-methylhexadecylamino)benzoyl]citric acid |
| 88 | 12 | Citric acid | O-[4-(dodecylamino)benzoyl]citric acid |
| 89 | 12 | Citric acid | O-[4-(2,4,6,8-tetramethylnonylamino)benzoyl]citric acid |
| 90 | 12 | Citric acid | O-[4-(1-ethyltetradecylamino)benzoyl]citric acid |
| 91 | 5 | α-Hydroxyisobutyric acid | α-[4-(1-methylpentadecylamino)benzoyloxy]isobutyric acid |
| 92 | 5 | α-Hydroxyisobutyric acid | α-[4-(hexadecylamino)benzoyloxy]isobutyric acid |

TABLE V

The following alkoxycarbonylalkyl and carbamoylalkyl 4-(alkylamino)benzoates are prepared by reacting the appropriate acyl chloride (chlorocarbonylalkyl 4-alkylaminobenzoate prepared by method of Example 6) with the noted alcohol or amine in the manner described in Example 7.

| Example | Starting Alcohol or Amine | Alkoxycarbonylalkyl or Carbamoylalkyl Ester Product |
|---|---|---|
| 95 | 1-Propanol | 1-(propoxycarbonyl)ethyl 4-(pentadecylamino)benzoate |
| 96 | Dimethylamine hydrochloride | 1-(dimethylcarbamoyl)ethyl 4-(pentadecylamino)benzoate |
| 97 | 1-Propanol | 1-(propoxycarbonyl)ethyl 4-(nonadecylamino)benzoate |
| 98 | Diethylamine hydrochloride | 1-(diethylcarbamoyl)ethyl 4-(nonadecylamino)benzoate |
| 99 | Dimethylaminoethanol | 2-(2-dimethylaminoethoxycarbonyl)-2-propyl 4-(1-heptylnonylamino)benzoate |
| 100 | 1-Propanol | 2-(propoxycarbonyl)-2-propyl 4-(1-heptylnonylamino)benzoate |
| 101 | Dimethylamine hydrochloride | 2-(dimethylcarbamoyl)-2-propyl 4-(1-heptylnonylamino)benzoate |
| 102 | Ethanol | 1-(ethoxycarbonyl)ethyl (1,4-diethyloctylamino)benzoate |
| 103 | Diethylamine hydrochloride | 1-(diethylcarbamoyl)ethyl 4-(15-methylhexadecylamino)benzoate |
| 104 | Methanol | 1-(methoxycarbonyl)ethyl 4-(15-methylhexadecylamino)benzoate |
| 105 | Ammonia | 1-(carbamoyl)ethyl 4-(13,13-dimethyltetradecylamino)benzoate |
| 106 | Ethanol | 1-(ethoxycarbonyl)ethyl 4-(13,13-dimethyltetradecylamino)benzoate |
| 107 | Diethylamine hydrochloride | 1-(diethylcarbamoyl)ethyl 4-(13,13-dimethyltetradecylamino)benzoate |
| 108 | 1-Propanol | 2-(propoxycarbonyl)-2-propyl 4-(1-methylpentadecylamino)benzoate |
| 109 | 2-Propanol | 2-(isopropoxycarbonyl)-2-propyl 4-(1-methylpentadecylamino)benzoate |
| 110 | Dimethylamine hydrochloride | 2-(dimethylcarbamoyl)-2-propyl 4-(1-methylpentadecylamino)benzoate |
| 111 | 2-Propanol | 2-(isopropoxycarbonyl)-2-propyl 4-(hexadecylamino)benzoate |
| 112 | Dimethylaminoethanol | 2-(2-dimethylaminoethoxycarbonyl)-2-propyl 4-(hexadecylamino)benzoate |
| 113 | Diethylamine hydrochloride | 2-(diethylcarbamoyl)-2-propyl 4-(hexadecylamino)benzoate |

TABLE VI

The following α-cyanoalkyl 4-(alkylamino)benzoates are prepared from the appropriate acyl chloride (prepared by the procedure described in Example 8) by treatment with the noted reagents:

| Example | Starting Aldehyde or Cyanohydrin | Method of Example | α-Cyanoalkyl 4-(Alkylamino)Benzoate Product |
|---|---|---|---|
| 117 | Formaldehyde | 17 | Cyanomethyl 4-(decylamino)benzoate |
| 118 | Acetone cyanohydrin | 3 | 2-cyano-2-propyl 4-(decylamino)benzoate |
| 119 | Acetaldehyde | 17 | 1-cyanoethyl 4-(tetradecylamino)benzoate |
| 120 | Propionaldehyde | 17 | 1-cyanopropyl 4-(pentadecylamino)benzoate |
| 121 | Acetone cyanohydrin | 3 | 2-cyano-2-propyl 4-(heptadecylamino)benzoate |
| 122 | Formaldehyde | 17 | Cyanomethyl 4-(1-methylpentadecylamino)benzoate |
| 123 | α-Methyl propionaldehyde | 17 | 1-cyano-2-methylpropyl 4-(1-methylpentadecylamino)benzoate |
| 124 | Acetaldehyde | 17 | 1-cyanoethyl 4-(1,4-diethyloctylamino)benzoate |
| 125 | Acetaldehyde | 17 | 1-cyanoethyl 4-(5,5-dimethylhexylamino)benzoate |
| 126 | Formaldehyde | 17 | Cyanomethyl 4-(5,5-dimethylhexylamino)benzoate |
| 127 | Acetone cyanohydrin | 3 | 2-cyano-2-propyl 4-(1,4-dimethyl-1-ethylhexylamino)benzoate |
| 128 | Formaldehyde | 17 | Cyanomethyl 4-(13,13-dimethyltetradecylamino)benzoate |
| 129 | Acetaldehyde | 17 | 1-cyanoethyl 4-(13,13-dimethyltetradecylamino)benzoate |
| 130 | Acetone cyanohydrin | 3 | 2-cyano-2-propyl 4-(13,13-dimethyltetradecylamino)benzoate |
| 131 | Formaldehyde | 17 | Cyanomethyl 4-(14-methylpentadecylamino)benzoate |
| 132 | Acetaldehyde | 17 | 1-cyanoethyl 4-(14-methylpentadecylamino)benzoate |

TABLE VII

The following α-carbamoylalkyl 4-(alkylamino)benzoates are prepared by hydrolysis of the corresponding α-cyanoalkyl 4-(alkylamino)benzoates according to Example 4.

| Example | Hydrolysis of Cyano Compound of Example | α-Carbamoylalkyl 4-(Alkylamino)Benzoate Product |
|---|---|---|
| 133 | 117 | Carbamoylmethyl 4-(decylamino)benzoate |
| 134 | 118 | 2-(carbamoyl)-2-propyl 4-(decylamino)benzoate |
| 135 | 119 | 1-(carbamoyl)ethyl 4-(tetradecylamino)benzoate |
| 136 | 120 | 1-(carbamoyl)propyl 4-(pentadecylamino)benzoate |
| 137 | 121 | 2-(carbamoyl)-2-propyl-(heptadecylamino)benzoate |
| 138 | 122 | Carbamoylmethyl 4-(1-methylpentadecylamino)benzoate |
| 139 | 123 | 1-(carbamoyl)-2-methylpropyl 4-(1-methylpentadecylamino)benzoate |
| 140 | 124 | 1-(carbamoyl)ethyl 4-(1,4-diethyloctylamino)benzoate |
| 141 | 125 | 1-(carbamoyl)ethyl 4-(5,5-dimethylhexylamino)benzoate |
| 142 | 126 | Carbamoylmethyl 4-(5,5-dimethylhexylamino)benzoate |
| 143 | 127 | 2-(carbamoyl)-2-propyl 4-(1,4-dimethyl-1-ethylhexylamino)benzoate |
| 144 | 128 | Carbamoylmethyl 4-(13,13-dimethyltetradecylamino)benzoate |
| 145 | 129 | 1-(carbamoyl)ethyl 4-(13,13-dimethyltetradecylamino)benzoate |
| 146 | 130 | 2-(carbamoyl)-2-propyl 4-(13,13-dimethyltetradecylamino)benzoate |
| 147 | 131 | Carbamoylmethyl 4-(14-methylpentadecylamino)benzoate |
| 148 | 132 | 1-(carbamoyl)ethyl 4-(14-methylpentadecylamino)benzoate |

TABLE VIII

The following esters of β-hydroxy acrylates are prepared by first activating the corresponding acid as described in Example 15, then treating the resulting acylating agents with the appropriate enol salts as described in Example 16 or 18.

| Example | Alkyl Group In 4-(Alkylamino)Benzoic Acid used | Method of Example | Enol-Forming β-Keto Compound Used | Alkoxycarbonylalkenyl 4-(Alkylamino)-Benzoate Product |
|---|---|---|---|---|
| 149 | Hexadecyl | 16 | Ethyl α-formylpropionate | 2-(ethoxycarbonyl)propenyl 4-(hexadecylamino)benzoate |
| 150 | Decyl | 16 | Ethyl α-formylpropionate | 2-(ethoxycarbonyl)propenyl 4-(decylamino)benzoate |
| 151 | Tridecyl | 16 | Ethyl α-formylpropionate | 2-(ethoxycarbonyl)propenyl 4-(tridecylamino)benzoate |
| 152 | Nonadecyl | 16 | Ethyl α-formylpropionate | 2-(ethoxycarbonyl)propenyl 4-(nonadecylamino)benzoate |
| 153 | 1-ethyltetradecyl | 16 | Ethyl α-formyl- | 2-(ethoxycarbonyl)propenyl 4-(1- |

TABLE VIII-continued

The following esters of β-hydroxy acrylates are prepared by first activating the corresponding acid as described in Example 15, then treating the resulting acylating agents with the appropriate enol salts as described in Example 16 or 18.

| Example | Alkyl Group In 4-(Alkylamino)Benzoic Acid used | Method of Example | Enol-Forming β-Keto Compound Used | Alkoxycarbonylalkenyl 4-(Alkylamino)-Benzoate Product |
|---|---|---|---|---|
| 154 | 13,13-dimethyltetradecyl | 16 | Ethyl α-formyl-propionate | 2-(ethoxycarbonyl)propenyl 4-(13,13-dimethyltetradecyl)benzoate |
| 155 | Nonyl | 16 | Ethyl α-formyl-acetate | 2-(ethoxycarbonyl)vinyl 4-(nonyl-amino)benzoate |
| 156 | Tetradecyl | 16 | Ethyl α-formyl-acetate | 2-(ethoxycarbonyl)vinyl 4-(tetradecylamino)benzoate |
| 157 | Octadecyl | 16 | Ethyl α-formyl-acetate | 2-(ethoxycarbonyl)vinyl 4-(octadecylamino)benzoate |
| 158 | 11-methyldodecyl | 16 | Ethyl α-formyl-acetate | 2-(ethoxycarbonyl)vinyl 4-(11-methyldodecylamino)benzoate |
| 159 | 5,5-dimethylhexyl | 16 | Ethyl α-formyl-acetate | 2-(ethoxycarbonyl)vinyl 4-(5,5-dimethylhexylamino)benzoate |
| 160 | 2,4,6,8-tetramethylnonyl | 16 | Ethyl α-formyl-acetate | 2-(ethoxycarbonyl)vinyl 4-(2,4,6,8-tetramethylnonylamino)benzoate |
| 161 | Decyl | 18 | Copper ethyl acetoacetate | 1-(ethoxycarbonyl)-2-propenyl 4-(decylamino)benzoate |
| 162 | Pentadecyl | 18 | Copper ethyl acetoacetate | 1-(ethoxycarbonyl)-2-propenyl 4-(pentadecylamino)benzoate |
| 163 | Heptadecyl | 18 | Copper ethyl acetoacetate | 1-(ethoxycarbonyl)-2-propenyl 4-(heptadecylamino)benzoate |
| 164 | 15,15-dimethylhexadecyl | 18 | Copper ethyl acetoacetate | 1-(ethoxycarbonyl)-2-propenyl 4-(15,15-dimethylhexadecylamino)-benzoate |
| 165 | 14-methylpentadecyl | 18 | Copper ethyl acetoacetate | 1-(ethoxycarbonyl)-2-propenyl 4-(14-methylpentadecylamino)benzoate |
| 166 | 1,4-diethyloctyl | 18 | Copper ethyl acetoacetate | 1-(ethoxycarbonyl)-2-propenyl 4-(1,4-diethyloctylamino)benzoate |
| 167 | 1-ethyltetradecyl | 18 | Copper ethyl acetoacetate | 1-(ethoxycarbonyl)-2-propenyl 4-(1-ethyltetradecylamino)benzoate |

TABLE IX

The following ethoxycarbonylalkyl 4-(alkylamino)benzoates are prepared by hydrogenation of the corresponding acrylates from Table VIII by application of the method described in Example 20.

| Example | Product |
|---|---|
| 168 | 2-(ethoxycarbonyl)propyl 4-(hexadecylamino)benzoate |
| 169 | 2-(ethoxycarbonyl)propyl 4-(decylamino)benzoate |
| 170 | 2-(ethoxycarbonyl)propyl 4-(tridecylamino)benzoate |
| 171 | 2-(ethoxycarbonyl)propyl 4-(nonadecylamino)benzoate |
| 172 | 2-(ethoxycarbonyl)propyl 4-(1-ethyltetradecylamino)benzoate |
| 173 | 2-(ethoxycarbonyl)propyl 4-(13,13-dimethyltetradecylamino)benzoate |
| 174 | 2-(ethoxycarbonyl)ethyl 4-(nonylamino)benzoate |
| 175 | 2-(ethoxycarbonyl)ethyl 4-(tetradecylamino)benzoate |
| 176 | 2-(ethoxycarbonyl)ethyl 4-(octadecylamino)benzoate |
| 177 | 2-(ethoxycarbonyl)ethyl 4-(11-methyldodecylamino)benzoate |
| 178 | 2-(ethoxycarbonyl)ethyl 4-(5,5-dimethylhexylamino)benzoate |
| 179 | 2-(ethoxycarbonyl)ethyl 4-(2,4,6,8-tetramethylnonylamino)benzoate |
| 180 | 1-(ethoxycarbonyl)-2-propyl 4-(decylamino)benzoate |
| 181 | 1-(ethoxycarbonyl)-2-propyl 4-(pentadecylamino)benzoate |
| 182 | 1-(ethoxycarbonyl)-2-propyl 4-(heptadecylamino)benzoate |
| 183 | 1-(ethoxycarbonyl)-2-propyl 4-(15,15-dimethylhexadecylamino)benzoate |
| 184 | 1-(ethoxycarbonyl)-2-propyl 4-(14-methylpentadecylamino)benzoate |
| 185 | 1-(ethoxycarbonyl)-2-propyl 4-(1,4-diethyloctylamino)benzoate |
| 186 | 1-(ethoxycarbonyl)-2-propyl 4-(1-ethyltetradecylamino)benzoate |

175

TABLE X

The following 4-(alkylamino)benzoyl derivatives of glyceric acid are prepared by the method of Example 19. The acyl chlorides necessary for the procedure are prepared by the method of Example 8.

| Example | 4-(Alkylamino)Benzoyl Derivative of Glyceric Acid Prepared |
|---|---|
| 187 | 3-O-[4-(octylamino)benzoyl]glyceric acid |
| 188 | 3-O-[4-(undecylamino)benzoyl]glyceric acid |
| 189 | 3-O-[4-(pentadecylamino)benzoyl]glyceric acid |
| 190 | 3-O-[4-(nonadecylamino)benzoyl]glyceric acid |
| 191 | 3-O-[4-(1-methylpentadecylamino)benzoyl]glyceric acid |
| 192 | 3-O-[4-(2-ethyldodecylamino)benzoyl]glyceric acid |
| 193 | 3-O-[4-(4,8,12-trimethyltridecylamino)benzoyl]glyceric acid |

TABLE X-continued

The following 4-(alkylamino)benzoyl derivatives of glyceric acid are prepared by the method of Example 19. The acyl chlorides necessary for the procedure are prepared by the method of Example 8.

| Example | 4-(Alkylamino)Benzoyl Derivative of Glyceric Acid Prepared |
|---|---|
| 194 | 3-O-[4-(15-methylhexadecylamino)benzoyl]glyceric acid |
| 195 | 3-O-[4-(13,13-dimethyltetradecylamino)benzoyl]glyceric acid |
| 196 | 3-O-[4-(5,5-dimethylhexylamino)benzoyl]glyceric acid |

TABLE XI

The following 3-pyridyl and phenyl esters of 4-(alkylamino)benzoic acids are prepared as described in Examples 22 or 24. The acyl chlorides for the method of Example 22 are prepared according to the method of Example 8.

| Example | Starting 3-Pyridinol or Phenol | Method of Example | Ester Product |
|---|---|---|---|
| 197 | 3-hydroxy-5-chloropyridine | 22 | 5-chloro-3-pyridyl 4-(nonylamino)benzoate |
| 198 | 3-hydroxy-5-methylpyridine | 24 | 4-methyl-3-pyridyl 4-(nonylamino)benzoate |
| 199 | 3-hydroxy-5-carboxypyridine | 22 | 5-carboxy-3-pyridyl 4-(nonylamino)benzoate |
| 200 | 3,6-dihydroxypyridine | 22 | 6-hydroxy-3-pyridyl 4-(undecylamino)benzoate |
| 201 | Phenol | 24 | Phenyl 4-(undecylamino)benzoate |
| 202 | 3-bromophenol | 24 | 3-bromophenyl 4-(undecylamino)benzoate |
| 203 | 4-(t-butoxycarbonyl)phenol | 24 | 4-(t-butoxycarbonyl)phenyl 4-(nonylamino)benzoate |
| 204 | 2-chloro-3-hydroxypyridine | 22 | 2-chloro-3-pyridyl 4-(tridecylamino)benzoate |
| 205 | 3-hydroxy-6-methylpyridine | 24 | 6-methyl-3-pyridyl 4-(tridecylamino)benzoate |
| 206 | 2,6-dimethyl-3-hydroxypyridine | 24 | 2,6-dimethyl-3-pyridyl 4-(pentadecylamino)benzoate |
| 207 | 2-methoxy-3-hydroxypyridine | 24 | 2-methoxy-3-pyridyl 4-(pentadecylamino)benzoate |
| 208 | 2,3-dihydroxypyridine | 24 | 2-hydroxy-3-pyridyl 4-(pentadecylamino)benzoate |
| 209 | 4-hydroxybenzoic acid | 22 | 4-carboxyphenyl 4-(tridecylamino)benzoate |
| 210 | 4-cyanophenol | 22 | 4-cyanophenyl 4-(pentadecylamino)benzoate |
| 211 | 3-hydroxy-5-chloropyridine | 24 | 5-chloro-3-pyridyl 4-(hexadecylamino)benzoate |
| 212 | 2-methyl-3-hydroxypyridine | 24 | 2-methyl-3-pyridyl 4-(hexadecylamino)benzoate |
| 213 | 2-methoxy-3-hydroxypyridine | 22 | 2-methoxy-3-pyridyl 4-(heptadecylamino)benzoate |
| 214 | 3-hydroxy-4-carboxypyridine | 22 | 4-carboxy-3-pyridyl 4-(heptadecylamino)benzoate |
| 215 | 2,6-dichlorophenol | 24 | 2,6-dichlorophenyl 4-(hexadecylamino)benzoate |
| 216 | 4-methoxycarbonylphenol | 24 | 4-methoxycarbonylphenyl 4-(hexadecylamino)benzoate |
| 217 | 3-methylphenol | 22 | 3-methylphenyl 4-(heptadecylamino)benzoate |
| 218 | 3-hydroxy-4-methylpyridine | 24 | 4-methyl-3-pyridyl 4-(1-heptylnonylamino)benzoate |
| 219 | 3-hydroxy-2-methoxypyridine | 24 | 2-methoxy-3-pyridyl 4-(1-heptylnonylamino)benzoate |
| 220 | 2,4-difluorophenol | 24 | 2,4-difluorophenyl 4-(1-heptylnonylamino)benzoate |
| 221 | 4-carboxamidophenol | 22 | 4-carboxamidophenyl 4-(1-heptylnonylamino)benzoate |
| 222 | 4-ethylphenol | 22 | 4-ethylphenyl 4-(1-heptylnonylamino)benzoate |
| 223 | 2-chloro-3-hydroxypyridine | 24 | 2-chloro-3-pyridyl 4-(1,4-diethyloctylamino)benzoate |
| 224 | 2-methoxy-3-hydroxypyridine | 24 | 2-methoxy-3-pyridyl 4-(1,4-diethyloctylamino)benzoate |
| 225 | 2,4-dichlorophenol | 24 | 2,4-dichlorophenyl 4-(1,4-diethyloctylamino)benzoate |
| 226 | 4-methylphenol | 22 | 4-methylphenyl 4-(1,4-diethyloctylamino)benzoate |
| 227 | 3-hydroxy-5-chloropyridine | 22 | 5-chloro-3-pyridyl 4-(5,5-dimethylhexylamino)benzoate |
| 228 | 3-hydroxy-6-methylpyridine | 24 | 6-methyl-3-pyridyl 4-(5,5-dimethylhexylamino)benzoate |
| 229 | Phenol | 24 | Phenyl 4-(5,5-dimethylhexylamino)benzoate |
| 230 | 2,6-dichlorophenol | 22 | 2,6-dichlorophenyl 4-(5,5-dimethylhexylamino)benzoate |
| 231 | 4-fluorophenol | 24 | 4-fluorophenyl 4-(5,5-dimethylhexylamino)benzoate |
| 232 | 3-hydroxypyridine | 22 | 3-pyridyl 4-(2,4,6,8-tetramethylnonylamino)benzoate |
| 233 | 3-hydroxy-6-methoxypyridine | 22 | 6-methoxy-3-pyridyl 4-(2,4,6,8-tetramethylnonylamino)benzoate |
| 234 | 2-bromophenol | 24 | 2-bromophenyl 4-(2,4,6,8-tetramethylnonylamino)benzoate |
| 235 | 2-ethylphenol | 24 | 2-ethylphenyl 4-(2,4,6,8-tetramethylnonylamino)benzoate |
| 236 | 4-chlorophenol | 24 | 4-chlorophenyl 4-(2,4,6,8-tetramethylnonylamino)benzoate |
| 237 | 2,6-dimethyl-3-hydroxy- | 22 | 2,6-dimethyl-3-pyridyl 4-(1,4-dimethyl-1-ethyl- |

TABLE XI-continued

The following 3-pyridyl and phenyl esters of 4-(alkylamino)benzoic acids are prepared as described in Examples 22 or 24. The acyl chlorides for the method of Example 22 are prepared according to the method of Example 8.

| Example | Starting 3-Pyridinol or Phenol | Method of Example | Ester Product |
|---|---|---|---|
| | pyridine | | hexylamino)benzoate |
| 238 | 2-carboxy-3-hydroxypyridine | 22 | 2-carboxy-3-pyridyl 4-(1,4-dimethyl-1-ethylhexylamino)benzoate |
| 239 | 2,4-difluorophenol | 24 | 2,4-difluorophenyl 4-(1,4-dimethyl-1-ethylhexylamino)benzoate |
| 240 | 4-(t-butoxycarbonyl)phenol | 24 | 4-(t-butoxycarbonyl)phenyl 4-(1,4-dimethyl-1-ethylhexylamino)benzoate |
| 241 | 3-hydroxy-6-chloropyridine | 24 | 6-chloro-3-pyridyl 4-(14-methylpentadecylamino)benzoate |
| 242 | 3-hydroxy-5-carboxypyridine | 22 | 5-carboxy-3-pyridyl 4-(14-methylpentadecylamino)benzoate |
| 243 | 2-methoxycarbonylphenyl | 22 | 2-methoxycarbonylphenyl 4-(14-methylpentadecylamino)benzoate |
| 244 | 2-bromophenol | 24 | 2-bromophenyl 4-(14-methylpentadecylamino)benzoate |
| 245 | Phenol | 24 | Phenyl 4-(14-methylpentadecylamino)benzoate |
| 246 | 3-hydroxy-4-methylphenol | 22 | 4-methyl-3-pyridyl 4-(15,15-dimethylhexadecylamino)benzoate |
| 247 | 3-hydroxy-6-carboxypyridine | 22 | 6-carboxy-3-pyridyl 4-(15,16-dimethylhexadecylamino)benzoate |
| 248 | 3-hydroxypyridine | 22 | 3-pyridyl 4-(15,15-dimethylhexadecylamino)benzoate |
| 249 | 3,6-dihydroxypyridine | 22 | 6-hydroxy-3-pyridyl 4-(15,15-dimethylhexadecylamino)benzoate |
| 250 | 4-cyanophenol | 24 | 4-cyanophenyl 4-(15,15-dimethylhexadecylamino)benzoate |
| 251 | 4-carboxamidophenol | 24 | 4-carboxamidophenyl 4-(15,15-dimethylhexadecylamino)benzoate |
| 252 | 2-ethylphenol | 24 | 2-ethylphenyl 4-(15,15-dimethylhexadecylamino)benzoate |

EXAMPLE 253

Preparation of 50 mg. Tablets

| Per Tablet | | Per 10,000 Tablets |
|---|---|---|
| 0.050 gm. | O-[4-(hexadecylamino)benzoyl]glycolic acid | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The O-[4-(hexadecylamino)benzoyl]glycolic acid, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 254

Preparation of Oral Suspension

| Ingredient | Amount |
|---|---|
| O$^3$-[4-(tetradecylamino)benzoyl]glyceric acid | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |

Preparation of Oral Suspension -continued

| Ingredient | | Amount |
|---|---|---|
| Distilled water | qs ad | 100 ml. |

The sorbitol solution is added to 40 ml. of distilled water and the O$^3$-[4-(tetradecylamino)benzoyl]glyceric acid is suspended therein. The saccharin, sodium benzoate, flavor and dye are added and dissolved. The volume is adjusted to 100 ml. with distilled water. Each ml. of syrup contains 5 mg. of O$^3$-[4-(tetradecylamino)benzoyl]glyceric acid.

EXAMPLE 255

Preparation of Ethyl α-ethyoxy-α[4-(hexadecylamino)benzoyloxy]-acetate

Into a mixture of 10 ml. of 1,2-dimethoxyethane and 5.8 ml. of ethanol is passed 3.65 g. hydrogen chloride gas with cooling. Then 10.2 g. of ethyl glyoxylate is added and after 24 hours at 25° C., 200 ml. of water and ice is added. The mixture is then extracted several times with ether and the extracts dried over anhydrous sodium sulfate. After evaporation of the extracts to an oil, the ethyl α-chloro-α-ethoxy-acetate so formed is added to a stirred mixture of 35.0 g. of sodium 4-(hexadecylamino)benzoate in 125 ml. of hexamethylphosphoramide. After 24 hours at 20° C., the product is obtained as white crystals by careful addition of water.

EXAMPLE 256

Preparation of 1-Ethoxyethyl 4-(hexadecylamino)benzoate

A mixture of 22.0 g. of ethyl 1-chloroethyl ether, 77.0 g. of sodium 4-(hexadecylamino)benzoate and 250 ml.

of hexamethylphosphoramide is stirred at 20° C. for 24 hours. After slow addition of water to the crystallization point and standing for 3 hours, the acetal ester is collected on a filter.

EXAMPLE 257

Preparation of Potassium sulfomethyl 4-(hexadecylamino)-benzoate

To 39.3 g. of potassium 4-(hexadecylamino)benzoate in 125 ml. of hexamethylphosphoramide is added 26.0 g. of powdered potassium iodomethanesulfonate. After stirring for 24 hours at 25° C., the product is obtained by careful dilution with water or alcohol to the crystallization point.

When this reaction is carried out with potassium 2-iodoethanesulfonate, the potassium sulfoethyl ester is obtained.

EXAMPLE 258

Preparation of 2-[4-(hexadecylamino)benzoyloxy]-5-methyltetrahydrofuran

In 50 ml. of 1,2-dimethoxyethane, 9.4 g. of N-trifluoroacetyl-4-(hexadecylamino)benzoyl chloride, 2.2 g. of triethylamine and 2.2 g. of 2-hydroxy-5-methyltetrahydrofuran are heated together at 60° C. for 24 hours. After addition at 30° C. of a small amount of aqueous potassium carbonate and standing for 4 hours, the white crystalline product is isolated by addition of water, filtration and recrystallization from acetonitrile.

EXAMPLE 259

Preparation of 1-[4-(Hexadecylamino)benzoyl]imidazole

A solution of 10 g. of 4-(hexadecylamino)benzoic acid, 10 ml. of pyridine and 4.0 g. of t-butylazidoformate in 100 ml. of dioxane is stirred for 18 hours at 20° C. Then 5.4 g. of 1,1'-carbonyldiimidazole is added and stirring continued for 20 hours. The solvents are evaporated to a thick oil which is dissolved in 100 ml. of hot chloroform, to which is added 5 ml. of trifluoroacetic acid. After 30 minutes at 55° C., the cooled solution is neutralized with diisopropylethylamine. The white product is crystallized from acetonitrile.

EXAMPLE 260

Preparation of α-ethoxy-α[4-(hexadecylamino)benzoyloxy]acetic acid

A solution of 4.1 g. of 1[4-(hexadecylamino)benzoyl]-imidazole and 1.2 g. of α-ethoxyglycolic acid in 30 ml. of 1,2-dimethoxyethane is heated at 40° C. for 5 hours. The corresponding acetal ester is isolated by dilution with cold water to the crystallization point.

EXAMPLE 261

Preparation of Sodium sulfoethyl 4-(hexadecylamino)benzoate

A mixture of 4.1 g. of 1-[4-(hexadecylamino)benzoyl]-imidazole and 1.5 g. of sodium 2-hydroxyethanesulfonate in 15 ml. of hexamethylphosphoramide is heated at 60° C. for 8 hours. The white crystalline product is obtained by adding ethanol till crystallization starts.

When 1.3 g. of sodium hydroxymethanesulfonate is employed in the above procedure, the sodium sulfomethyl ester is obtained.

I claim:
1. A compound of the formula:

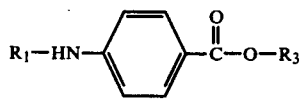

wherein $R_1$ is an unbranched or branched alkyl group of the formula $C_nH_{2n+1}$ wherein n is an integer from 8 to 19, inclusive, and $R_3$ is 3-pyridyl, 5-methyl-3-pyridyl, 2,6-dimethyl-3-pyridyl, 6-methoxy-3-pyridyl, 2-hydroxy-3-pyridyl, 6-chloro-3-pyridyl, 4-carboxy-3-pyridyl, 5-carboxy-3-pyridyl or 4-cyano-3-pyridyl; and the pharmaceutically acceptable acid-addition and cationic salts thereof.

2. The compound according to claim 1; 3-pyridyl 4-(hexadecylamino)benzoate.

3. The compound according to claim 1; 6-chloro-3-pyridyl 4-(hexadecylamino)benzoate.

4. The compound according to claim 1; 2,6-dimethyl-3-pyridyl 4-(hexadecylamino)benzoate.

5. The compound according to claim 1; 5-carboxy-3-pyridyl 4-(hexadecylamino)benzoate.

6. The compound according to claim 1; 2-hydroxy-3-pyridyl 4-(hexadecylamino)benzoate.

7. The compound of treating hyperlipidemia and hyperlipoproteinemia and/or altering the lipoprotein pattern in a mammal comprising administering to said mammal an effective lipid-altering amount of a compound in accordance with claim 1.

* * * * *